(12) United States Patent
Marnfeldt

(10) Patent No.: US 10,819,713 B2
(45) Date of Patent: Oct. 27, 2020

(54) TECHNIQUE TO ENSURE SECURITY FOR CONNECTED IMPLANTABLE MEDICAL DEVICES

(71) Applicant: Boston Scientific Neuromodulation Corporation, Valencia, CA (US)

(72) Inventor: Goran Marnfeldt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 245 days.

(21) Appl. No.: 15/914,490

(22) Filed: Mar. 7, 2018

(65) Prior Publication Data

US 2018/0309766 A1    Oct. 25, 2018

Related U.S. Application Data

(60) Provisional application No. 62/489,209, filed on Apr. 24, 2017.

(51) Int. Cl.
*H04L 29/06*    (2006.01)
*G16H 40/40*    (2018.01)
(Continued)

(52) U.S. Cl.
CPC ........ *H04L 63/108* (2013.01); *A61N 1/37254* (2017.08); *A61N 1/37264* (2013.01); *G06F 8/61* (2013.01); *G06F 8/65* (2013.01); *G06F 8/654* (2018.02); *G06F 21/572* (2013.01); *G16H 40/40* (2018.01); *G16H 40/67* (2018.01); *H04L 9/0891* (2013.01); *H04L 9/3226* (2013.01); *H04L 9/3297* (2013.01); *H04L 63/0853* (2013.01); *H04L 67/12* (2013.01); *H04W 4/80* (2018.02);
(Continued)

(58) Field of Classification Search
CPC ...................................................... H04L 67/12
See application file for complete search history.

(56) References Cited

U.S. PATENT DOCUMENTS 8,335,569 B2    12/2012    Aghassian
8,498,716 B2    7/2013    Chen et al.
(Continued)

OTHER PUBLICATIONS

U.S. Appl. No. 62/386,000, filed Sep. 10, 2016, Weiss et al.
(Continued)

*Primary Examiner* — Jason K Gee
(74) *Attorney, Agent, or Firm* — Lewis & Reese, PLLC

(57) ABSTRACT

An implantable medical device (IMD) includes communication circuitry that enables the IMD to communicate via a network such as the Internet. A security routine is executed on the IMD to determine whether the IMD is capable over communicating via the network. If so, the IMD requests an identifier of current firmware stored on a server that is connected to the communication network. The identifier of the current firmware is compared to an identifier of firmware that is installed on the IMD. If the installed firmware is the same as the current firmware on the server, a timer is reset, but if the installed firmware cannot be verified as matching the current firmware on the server (e.g., because the IMD is not capable of communicating via the network), the timer continues to run. When the timer expires, the IMD is prevented from communicating via the network until further action is taken.

18 Claims, 5 Drawing Sheets

(51) Int. Cl.
- *H04W 4/80* (2018.01)
- *G06F 8/65* (2018.01)
- *A61N 1/372* (2006.01)
- *G06F 8/61* (2018.01)
- *G16H 40/67* (2018.01)
- *H04L 9/08* (2006.01)
- *H04L 9/32* (2006.01)
- *H04L 29/08* (2006.01)
- *G06F 8/654* (2018.01)
- *G06F 21/57* (2013.01)
- *H04W 12/06* (2009.01)
- *H04W 12/08* (2009.01)
- *H04B 5/00* (2006.01)

(52) U.S. Cl.
CPC ....... *H04W 12/06* (2013.01); *H04W 12/0804* (2019.01); *H04W 12/0808* (2019.01); *H04B 5/0075* (2013.01); *H04L 67/34* (2013.01); *H04L 2209/88* (2013.01)

(56) References Cited

U.S. PATENT DOCUMENTS

| | | | |
|---|---|---|---|
| 8,706,251 | B2 | 4/2014 | Von Arx et al. |
| 8,768,453 | B2 | 7/2014 | Parramon et al. |
| 8,868,201 | B2 | 10/2014 | Roberts et al. |
| 8,983,615 | B2 | 3/2015 | Tahmasian et al. |
| 9,269,251 | B2 | 2/2016 | Lalonde et al. |
| 2003/0046677 | A1 | 3/2003 | Lindberg et al. |
| 2004/0073276 | A1* | 4/2004 | Samuelsson ....... A61N 1/37211 607/60 |
| 2005/0204134 | A1 | 9/2005 | Von Arx et al. |
| 2007/0167151 | A1* | 7/2007 | Zinn ....... H04W 4/12 455/411 |
| 2008/0319497 | A1 | 12/2008 | Griffith et al. |
| 2011/0015693 | A1* | 1/2011 | Williamson ....... A61N 1/37252 607/30 |
| 2012/0095529 | A1 | 4/2012 | Parramon et al. |
| 2015/0073500 | A1 | 3/2015 | Kothandaraman |
| 2015/0080982 | A1 | 3/2015 | Funderburk |

OTHER PUBLICATIONS

U.S. Appl. No. 62/393,003, filed Sep. 10, 2016, Weerakoon et al.
"Cybersecurity," U.S. Food and Drug Administration, obtained on Mar. 20, 2017, 4 pages, obtained from <http://www.fda.gov/medicaldevices/DigitalHealth/ucm373213.htm>.
Marin, Eduard, et al., "On the (In)security of the Latest Generation Implantable Cardiac Defibrillators and How to Secure Them," Proceedings of the 32nd Annual Conference on Computer Security Applications, Dec. 5-8, 2016, pp. 226-236.
"Postmarket Management of Cybersecurity in Medical Devices—Guidance for Industry and Food and Drug Administration Staff," U.S. Department of Health and Human Services—Food and Drug Administration, Dec. 28, 2016, 30 pages.
Williams, Patricia AH, et al., "Cybersecurity Vulnerabilities in Medical Devices: A Complex Environment and Multifaceted Problem," Medical Devices: Evidence and Research, 2015:8, Jul. 20, 2015, pp. 305-316.
International Search Report and Written Opinion regarding corresponding PCT Application No. PCT/US2018/021529, dated Jun. 14, 2018.

* cited by examiner

TECHNIQUE TO ENSURE SECURITY FOR CONNECTED IMPLANTABLE MEDICAL DEVICES

CROSS-REFERENCE TO RELATED APPLICATIONS

This is a non-provisional application of U.S. Provisional Patent Application Ser. No. 62/489,209, filed Apr. 24, 2017, to which priority is claimed, and which is incorporated herein by reference in its entirety.

FIELD OF THE TECHNOLOGY

The present application relates to a technique for ensuring the security of connected implantable medical devices that are capable of communicating via communication networks such as the Internet.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The present disclosure may find applicability with any Implantable Medical Device (IMD) or in any IMD system.

As shown in FIG. 1, an IMD 10 includes a biocompatible device case 12 that is formed from a metallic material such as titanium. The case 12 typically comprises two components that are welded together, and it holds the circuitry and battery 14 (FIG. 2) necessary for the IMD 10 to function, which battery 14 may be either rechargeable or primary (non-rechargeable) in nature. The IMD 10 is coupled to electrodes 16 via one or more electrode leads 18 (two of which are shown). The proximal ends of the leads 18 include electrode terminals 20 that are coupled to the IMD 10 at one or more connector blocks 22 fixed in a header 24, which can comprise an epoxy for example. Contacts in the connector blocks 22 make electrical contact with the electrode terminals 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary.

As shown in FIG. 2, IMD 10 contains a charging coil 30 for wireless charging of the IMD's battery 14 using an external charging device 50, assuming that battery 14 is a rechargeable battery. If IMD 10 has a primary battery 14, charging coil 30 in the IMD 10 and external charger 50 can be eliminated. IMD 10 also contains a telemetry coil antenna 32 for wirelessly communicating data with an external controller device 40, which is explained further below. In other examples, antenna 32 can additionally or alternatively include a short-range RF antenna such as a slot, patch, or wire antenna. Furthermore, the IMD has a magnetic sensor 33 to detect the presence of an external magnetic field. This sensor can be used to turn off therapy in an emergency situation, or to command the IMD into particular modes of operation such as MRI mode. IMD 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IMD 10, in plan and cross section views. External controller 40 may be used to control and monitor the IMD 10 via a bidirectional wireless communication link 42 passing through a patient's tissue 5. For example, the external controller 40 may be used to provide or adjust a stimulation program for the IMD 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IMD 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-held, portable housing. The magnetic sensor 33 can also act as a very basic form of communication receiver, e.g. to detect the presence of an external permanent magnet in order to alter the operating mode of the IMD.

External charger 50 provides power to recharge the IMD's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IMD 10, which is rectified, filtered, and used to recharge the battery 14. Link 52, like link 42, can be bidirectional to allow the IMD 10 to report status information back to the external charger 50, such as by using Load Shift Keying as is well-known. For example, once circuitry in the IMD 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

While a standard external controller 40 is illustrated in FIG. 2, more recent generations of IMDs are becoming more "connected" in the sense that they are also capable of communicating with other types of external devices, some of which enable connectivity between the IMD 10 and a broader network such as the Internet. This disclosure addresses security concerns that arise as a result of the accessibility of IMDs via far-reaching networks.

DETAILED DESCRIPTION

Figure 1:
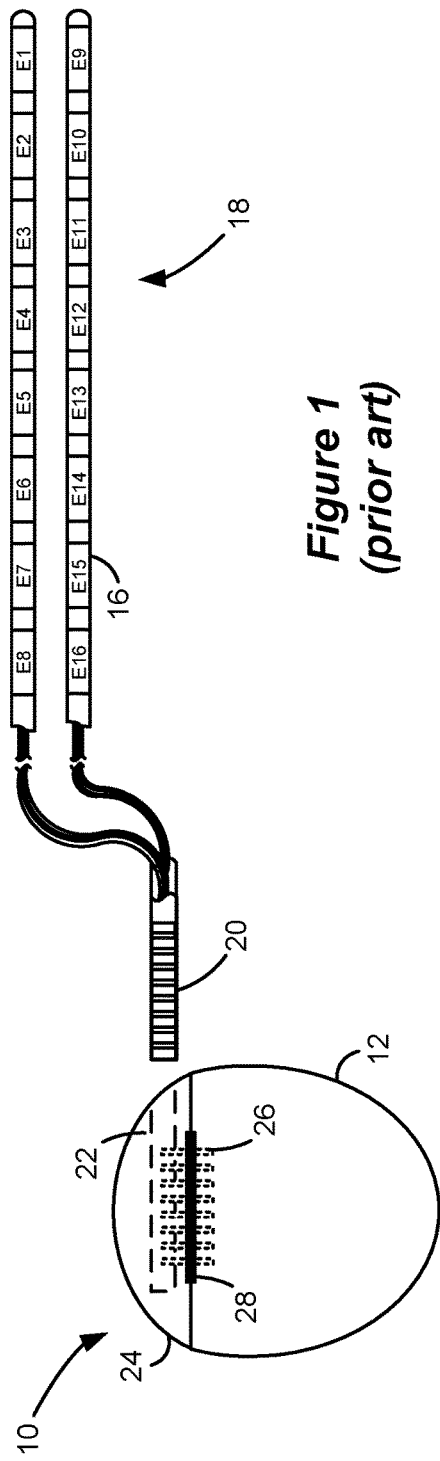
FIG. 1 shows an implantable medical device (IMD), in accordance with the prior art.
Figure 2:
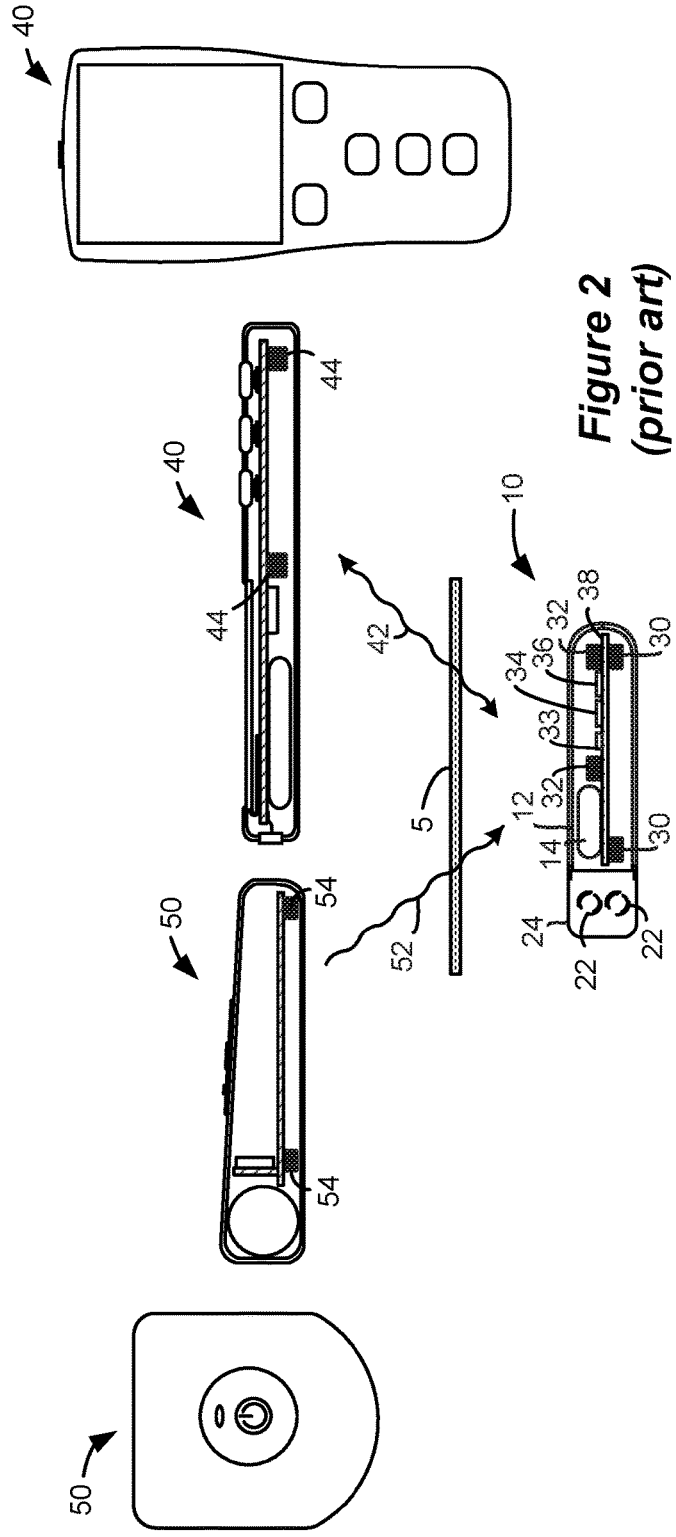
FIG. 2 shows a cross section of the IMD of FIG. 1 as implanted in a patient, as well as external devices that support the IMD, including an external charger and external controller, in accordance with the prior art.
Figure 3:
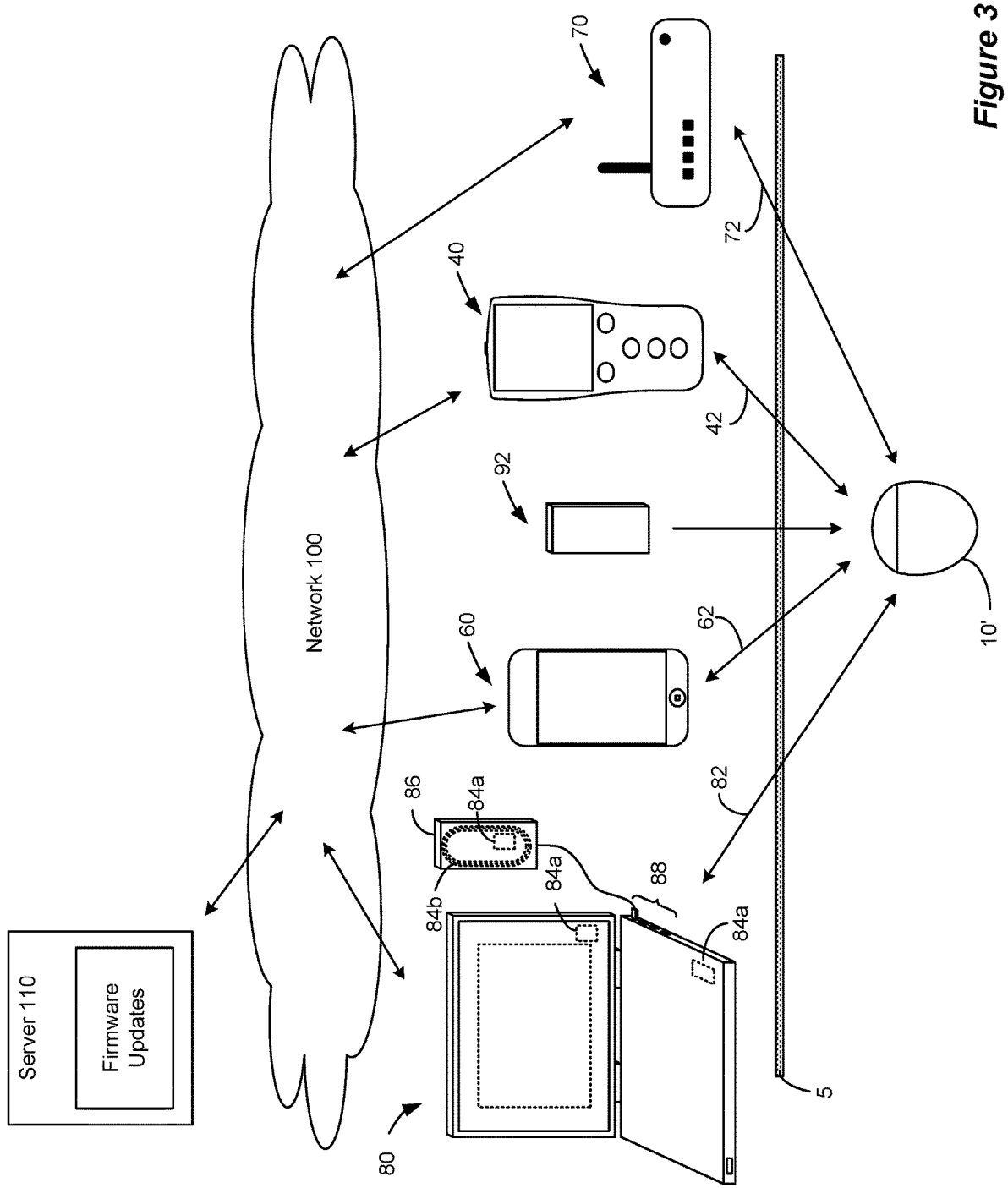
FIG. 3 shows an IMD in communication with various external devices, including external devices that enable network connectivity of the IMD in accordance with an aspect of the disclosure.

FIG. 3 illustrates the various types of external devices with which an IMD 10' may be capable of communicating. The IMD 10' may be configured to communicate with a clinician's programming system ("CP System") 80 via a link 82. The clinician's programming system 80 may be a desktop, laptop, or notebook computer, a tablet, a Personal Data Assistant (PDA)-type mobile computing device, etc. Communications on link 82 may occur via magnetic inductive coupling (e.g., FSK) or short-range RF telemetry (e.g., Bluetooth, WiFi, Zigbee, MICS, etc.) through an integrated short-range RF antenna 84a or an accessory communication head 86 that includes a short-range RF antenna 84a and/or a coil antenna 84b and that is connectable to a port 88 of the CP system 80.

The IMD 10' may additionally be configured to communicate with a personal electronics device such as a mobile phone 60. In the illustrated embodiment, the IMD 10' communicates with the mobile phone 60 via a link 62, which may typically comprise a short-range RF telemetry link. Like the IMD 10 described above, the IMD 10' may also communicate with the external controller 40 via a link 42, which may comprise a magnetic inductive coupling link or a short-range RF telemetry link. The CP System 80, mobile phone 60, and external controller 40 may each execute software that provides an interface through which a user may monitor and control the IMD 10'.

The IMD 10' may also be capable of communicating directly with a wireless router 70, a bedside monitoring system, a base station, or a similar type of access point via a link 72, which may typically comprise a short-range RF telemetry link. While a device such as the wireless router 70 may not provide a direct interface through which a user can monitor and control the IMD 10', it provides a connection between the IMD 10' and a network 100, such as the Internet, which enables another device, such as one of the other types of external devices (e.g., CP system 80, mobile phone 60, or external controller 40) to monitor and control the IMD 10' via a connection to the network 100. Thus, an external device such as the CP system 80, mobile phone 60, or external controller 40 may monitor and control the IMD 10' over the network 100 without establishing a direct connection to the IMD 10'. In fact, each of the CP system 80, mobile phone 60, external controller 40, and wireless router 70 may act as an access point that facilitates communication between the IMD 10 and another device connected to the network 100 via the external device's connection to the network 100.

By contrast, the external magnet 92 may act as a very simplistic way of communicating unidirectionally to the IMD 10' (e.g., to change the mode of operation of the IMD 10') over a short distance through the detection of the magnet 92 by the magnetic sensor 33. The magnet 92 can be either a permanent magnet or a solenoid driven by a power source, which power source can be modulated by e.g. a PCM (Pulse Code Modulated) signal in order to transmit a simple command.

The enhanced connectivity of IMD 10' provides great benefits to patients and clinicians. For example, an Internet-connected IMD can be evaluated and/or reconfigured by a clinician from practically anywhere in the world with an Internet connection. Thus, for example, a clinician may retrieve the stimulation history from a patient's IMD 10 and readjust the stimulation program while the clinician is in her office and the patient is in his home. However, this increased convenience is accompanied by increased risk. For example, just as a clinician may adjust the parameters of the IMD 10' from around the world, a malicious actor may exploit a vulnerability in an IMD's firmware to perform such bad acts as retrieving confidential information or, worse yet, interacting with the IMD 10' in a way that causes harm to the patient. The manufacturer of the IMD 10' can mitigate these risks by distributing firmware updates to IMDs 10' to patch identified vulnerabilities. For example, the manufacturer of the IMD 10' may maintain a computing device such as a server 110 on which the manufacturer stores firmware updates such that the firmware may be obtained by IMDs 10' over the network 100. As used herein, firmware refers to software or program code that affects the operation of the IMD 10'.

Firmware updates that are distributed by a manufacturer of the IMD 10' may seek to address various different types of vulnerabilities. For example, a firmware update may correct a vulnerability that enables a malicious actor to circumvent the intended functionality of the hardware of the IMD 10'. For example, such a firmware update may correct a vulnerability that enables a malicious actor to prevent a component of the IMD 10' from going into a low-energy mode as intended. Another firmware update may add or change the firewall functionality of the IMD 10' to prevent unauthorized access to the IMD 10'. For example, such an update may add or alter packet and/or stateful filtering rules in the firewall functionality of the IMD 10'. Still another firmware update may add or alter rules that define the types of therapy or operational mode adjustments that may be made on the IMD 10', e.g., from a device that is accessing the IMD 10' via the network 100. Examples of these types of therapy and operational mode rules are described in U.S. Patent Publication No. 2015/0073500, which is incorporated herein by reference.

While IMD manufacturers are motivated to identify and eliminate vulnerabilities in their devices, even the most diligent efforts are limited by the ability to distribute updates to affected IMDs 10'. If an IMD 10' is unreachable over the network 100, it cannot receive an update, and its vulnerability will remain exploitable. In fact, the distribution of an update may alert malicious actors to the vulnerability and increase the likelihood that the vulnerability is exploited on IMDs 10' that do not receive the update. This disclosure provides a technique for ensuring the continued security of connected IMDs 10'.

Figure 4:
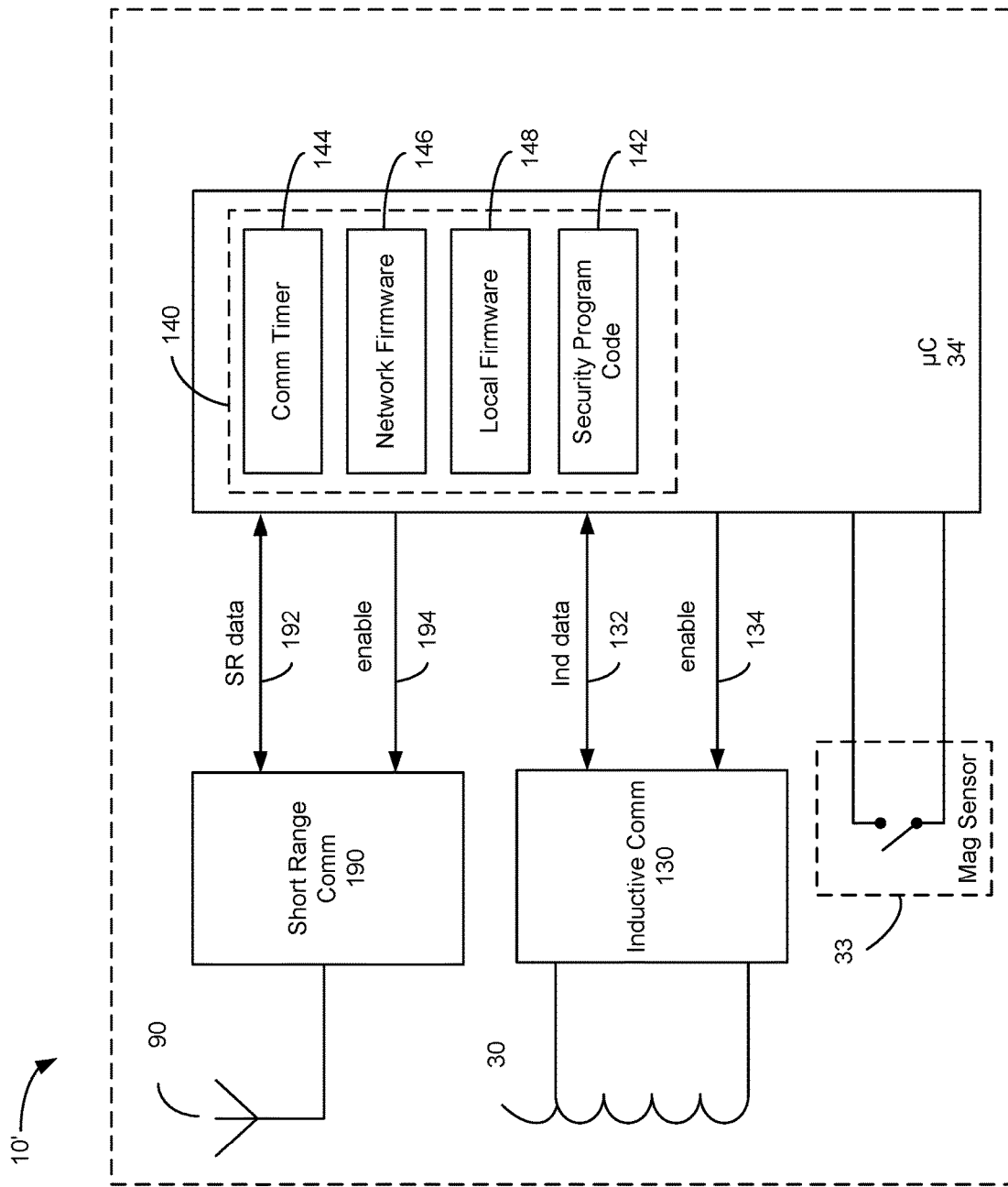
FIG. 4 is a block diagram showing various components of the IMD in accordance with an aspect of the disclosure.

FIG. 4 is a block diagram that illustrates various components of the IMD 10', which is configured to implement the disclosed security technique. The IMD 10' includes control circuitry (e.g., microcontroller 34') that provides master control over the operations (including communications with external devices) of the IMD 10'. While described herein as a microcontroller 34', the control circuitry can comprise a microcontroller, microprocessor, Field Programmable Gate Array, Programmable Logic Device, Digital Signal Processor or like devices. In one specific example, control circuitry can comprise or include an MSP430 microcontroller device, manufactured by Texas Instruments, Inc. Control circuitry may also be based on other well-known low-power microcontroller technology. Control circuitry may include a central processing unit capable of executing program code to cause the control circuitry to perform the steps of the security routine 200 described below, with such instructions stored in volatile or non-volatile memory within the control circuitry. Control circuitry may also include, operate in conjunction with, or be embedded within an Application Specific Integrated Circuit (ASIC), such as described in U.S. Patent Application Publications 2008/0319497 or 2012/0095529, or U.S. Provisional Patent Applications 62/386,000 or 62/393,003, both filed Sep. 10, 2016. The control circuitry may comprise an integrated circuit with a monocrystalline substrate, or may comprise any number of such integrated circuits. Control circuitry may also be included as part of a System-on-Chip (SoC) or a System-on-Module (SoM) which may incorporate memory devices and other digital interfaces.

The microcontroller 34' interfaces with short-range RF communication circuitry 190, inductive communication circuitry 130, and the magnetic sensor 33 in the IMD 10'. The communication circuitry in the IMD 10' enables the IMD 10' to communicate via the network 100. As described above, the inductive communication circuitry 130 may include circuitry that operates in conjunction with the coil 32 to communicate via a magnetic inductive coupling link using a protocol such as FSK. Similarly, the short-range RF communication circuitry 190 may include circuitry that operates in conjunction with the antenna 90 to communicate via a short-range RF link using a protocol such as Bluetooth, WiFi, Zigbee, MICS, etc. Similarly, the magnetic sensor 33 monitors for the presence of a static (or low rate on/off modulated) magnetic field (e.g., a magnetic field generated by the magnet 92). While short-range RF communication circuitry 190, inductive communication circuitry 130, and the magnetic sensor 33 are illustrated, some embodiments of the IMD 10' may not include all of these components.

The microcontroller 34' enables and disables the short-range RF communication circuitry 130 and the inductive communication circuitry 190 via the enable signals 134 and 194, respectively. The control signals 194 and 134 may be routinely used to periodically enable the short-range RF communication circuitry 194 and inductive communication circuitry 134 to "listen" for any communications. The communication circuitry, which is relatively energy intensive, may otherwise be disabled so as to conserve energy in the IMD 10'. The magnetic sensor is monitored continuously. When communication circuitry (either short-range RF communication circuitry 190 or inductive communication circuitry 130) is enabled, the microcontroller 34' additionally passes data to and receives data from the enabled communication circuitry via the data buses 192 and 132. Data received at either the antenna 90 or the coil 30 is demodulated and communicated via the buses 192 and 132. Likewise, data communicated from the microcontroller 34' to the communication circuitry via the buses 192 and 132 is modulated and communicated using the antenna 90 or the coil 30. The presence of a static (or low rate on/off modulated) magnetic field can either control the stimulation hardware directly, be monitored (and demodulated if carrying modulated information) by the microcontroller 34', or both.

The microcontroller 34' includes memory 140 that stores security program code 142 that, when executed, cause the microcontroller 34' to implement the security routine 200 described below. The memory 140 additionally stores parameters that are used during execution of the security program code 142 (i.e., communications timer parameters 144, network firmware identifier 146, local firmware identifier 148, etc.).

Figure 5:
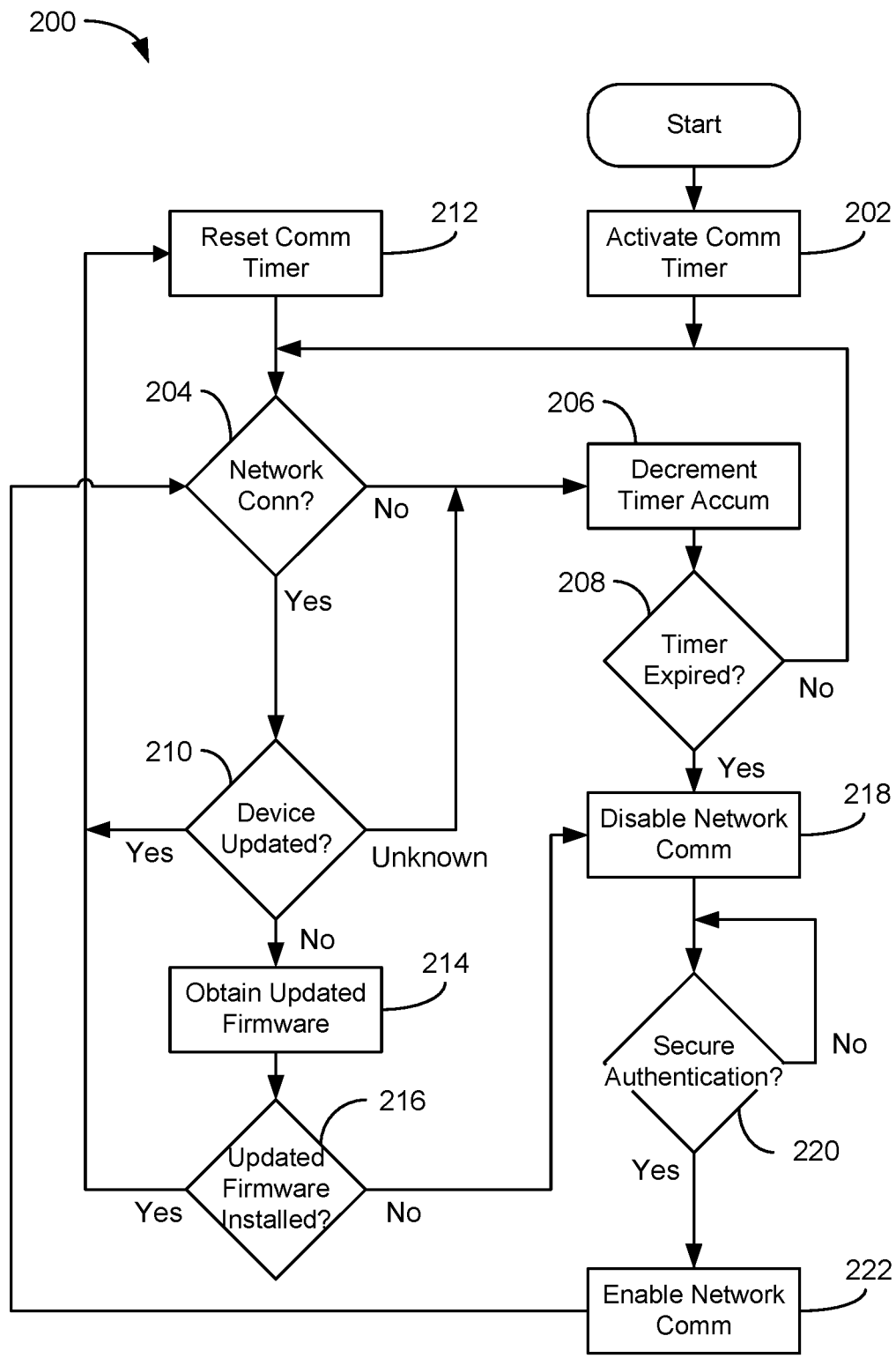
FIG. 5 is a flowchart that shows the steps of a security routine in accordance with an aspect of the disclosure.

FIG. 5 is a flowchart that illustrates the functionality of the security routine 200. When the IMD 10' is initialized (e.g., after implantation), a communications timer is activated (202). The activation of the communications timer initiates a countdown from a preset time value (e.g., 30 days) during which the IMD 10' must communicate via the network 100 over which it can receive security updates. The communications timer may have several parameters (e.g., preset value, current value, enabled bit, expired bit, etc.) that are stored in the communication timer parameters 144 of the memory 140.

Following activation of the timer, it is determined whether the IMD 10' is capable of communicating via the network 100 (204). This determination can be made in different manners. In a first embodiment, the microprocessor 34' may evaluate whether a particular communication port (e.g., a TCP, SCTP, or UDP port) that is used by the IMD 10' to communicate over the network 100 is open. If the port is open, it may be determined that the IMD 10' is capable of communicating via the network 100.

In another embodiment, the microprocessor 34' may send a request to the server 110, which is only reachable over the network 100. If a response is received from the server 110, it may be determined that the IMD 10' is capable of communicating via the network 100. In one embodiment, the request may be a request for an identifier 146 of the current firmware for the particular model of the IMD 10'. The identifier 146 may be any data that identifies the current firmware that is available on the server 110. For example, the identifier 146 may be a hash of the current firmware, a version number of the current firmware, etc. Communications between the IMD 10' and the server 110 may be encrypted or otherwise structured in a manner that enables the IMD 10' to verify that a received response is actually from the server 110.

In one embodiment, the attempted communication with the server 110 may be performed asynchronously with the execution of the security routine 200. For example, the microprocessor 34' may periodically request information from the server 110 and, if a response is received, it may be timestamped and stored, e.g., in the memory 140. Upon the subsequent execution of the routine 200, the timestamped response can be evaluated to determine whether the IMD 10' has recently communicated via the network 100. In such an embodiment, a stored response may only be considered to indicate that the IMD 10' is capable of communicating via the network 100 if the timestamped response was received within a predetermined time period (e.g., within the previous five minutes).

If the IMD 10' is not capable of communicating via the network 100, the communications timer continues to run and the remaining time is decremented (206) by the amount of time that has passed since the last timer update. For example, if 10 minutes have passed since the last execution of the security routine 200, the remaining time is decremented by 10 minutes. If the timer has not timed out (i.e., if the remaining time value is greater than zero) (208), the microcontroller 34' continues to monitor for connectivity to the network 100 (204). While the communication timer is described as being decremented, it will be understood that other timers, such as a timer that is incremented may also be utilized.

If it is determined that the IMD 10' is (or has recently been) capable of communicating via the network 100, it is then determined whether the most current firmware has been installed on the IMD 10' (210). In order to make this determination, the microprocessor 34' may request that the server 110 provide the identifier 146 of the most current firmware for the particular model of the IMD 10'. This request may include a model number, a serial number, or some other identifier of the requesting IMD 10' to allow the server 110 to identify the correct current firmware identifier 146 for the IMD 10'. The identifier 146 that is received from the server 110 may be stored in the memory 140.

Alternatively, if a response from the server 110 served as the basis for the determination that the IMD 10' is capable of communicating via the network 100, the response may have included the identifier 146, and thus the identifier 146 may already be stored in the memory 140. If so, the stored identifier 146 can be used in lieu of requesting the identifier 146 from the server 110. In any event, the identifier 146 received from the server 110 is compared to the identifier 148 of the firmware that is installed on the IMD 10', which identifier 148 is also stored in the memory 140. Like the identifier 146, the identifier 148 of the firmware installed on the IMD 10' can include any data that represents the firmware that is installed on the IMD 10'.

If the identifier of the local firmware 148 matches the identifier of the network firmware 146, it is determined that the most current firmware is installed on the IMD 10', and the network communication timer is reset to the original preset value (212).

In some cases, the microprocessor 34' may not be able to determine whether the IMD 10' has the most current firmware. For example, even though the IMD 10' may be (or may have recently been) capable of communicating via the network 100, the IMD 10' may not be able to receive a response from the server 110 with an identifier 146 of the most current firmware. If it cannot be positively determined whether or not the most current firmware is installed on the IMD 10', the communications timer continues to run (206) and, unless the communications timer has expired, the microcontroller 34' continues to monitor for network connectivity (204).

If the identifier of the local firmware 148 does not match the identifier of the network firmware 146 received from the server 110, it is determined that the IMD 10' does not have the most current firmware. Because this indicates a potential security vulnerability, the IMD 10' immediately attempts to obtain the most current firmware from the server 110 (214). The firmware may be obtained from the server 110 by sending a request to the server 110 that includes both the identifier of the local firmware 148 as well as the identifier 146 of the most current firmware that the IMD 10' needs to install. As will be understood, it may be necessary for the IMD 10' to obtain and install any intervening versions of the firmware, and so such a request can inform the server 110 as to the versions of the firmware that are needed by the IMD 10'.

The microcontroller 34' may download the updated firmware from the server 110 via its connection to the network 100 and install the firmware without any user interaction. In another embodiment, the IMD 10' may attempt to communicate with an external device (e.g., external controller 40, phone 60, clinicians programmer 80, etc.) via a direct connection to the external device to cause the external device to present a security warning to the user and to prompt the user to approve the download and installation of the most current firmware. In such an embodiment, upon user approval, the firmware is downloaded and installed by the IMD 10' either through the external device or another connection to the server 110.

If the updated firmware is obtained and installed on the IMD 10' (216), the communication timer is reset in the same manner as when it is determined that the most current firmware is installed on the IMD 10' as described above. The identifier of the updated firmware that is now installed on the IMD 10' is also stored in the memory 140. If, however, after determining that the most current firmware is not installed on the IMD 10', the firmware cannot be obtained and installed on the IMD 10', or if the communications timer expires (i.e., the remaining time value is equal to zero), the microcontroller 34' prevents the IMD 10' from communicating via the network 100 (218). In this way, the security routine 200 prevents the exploitation of potential vulnerabilities in two scenarios: 1) when it is determined that the firmware installed on the IMD 10' is out of date and the updated firmware cannot be installed and 2) when the IMD 10' has not connected to the network 100 within a reasonable time period such that it cannot be ascertained whether the firmware installed on the IMD 10' is out of date. The latter protection prevents the IMD 10' from being exploited when it reconnects to the network 100 after a long period of no connectivity, because the IMD may likely have out of date firmware.

The microcontroller 34' can prevent the IMD 10' from communicating via the network 100 in different manners. In a first embodiment, the microcontroller 34' may prevent the IMD 10' from communicating via the network 100 through untrusted third party access points such as wireless router 70. For example, the microcontroller 34' may disable a communication port (e.g., a TCP, SCHP, or UDP port) that is used by the IMD 10' to communicate via the network 100 through such untrusted access points. In another embodiment, the microcontroller 34' may completely disable non-inductive communications. For example, the microcontroller may disable short-range RF communication circuitry 190 via control signal 194. In yet another embodiment, the microcontroller 34' may disable both inductive communication circuitry 130 and short-range RF communication circuitry 190 via control signals 134 and 194, respectively.

Regardless of the manner in which the microcontroller prevents the IMD 10' from communicating via the network 100, any vulnerabilities of the IMD 10' are substantially reduced or eliminated because the IMD 10' can only be accessed via the network through devices that are considered to be trusted. Thus, a malicious actor with the ability to communicate via the network 100 will be unable to access the IMD 10'.

In order to re-establish communications via the network 100, a secure authentication process must be performed (220). The type of authentication process that is required depends on the manner in which communications via the network 100 are prevented. For example, if communications are prevented by disabling a communications port used to communicate with an untrusted third party device such as wireless router 70, the secure authentication may be performed through a communication with a "trusted" device. The trusted device may be a device that communicates with the IMD 10' using inductive-based communications (e.g., the external controller 40 or CP system 80). Inductive communications can be considered to be secure because they can only be conducted over a very short distance (e.g., less than 3 feet). Thus, it can be virtually guaranteed that communications received via inductive communication circuitry 130 are not from a malicious actor because they must be transmitted from a device that is in close proximity to the IMD 10' and, thus, the patient. The trusted device may also be a device that communicates via short-range RF telemetry such as mobile phone 60 or CP system 80. While short-range RF telemetry does not provide the same proximity security as do inductive communications, the communicating devices may be determined to be trusted in other ways. For example, the mobile phone 60 may be trusted if it can be determined by the microcontroller 34' that the phone 60 has previously communicated with the IMD 10'. Alternatively, the external magnet 92 may be placed in proximity to the IMD 10' while using short-range RF telemetry to provide the proximity security (assuming the valid user looks around to determine no malicious person is within "short-range"). Regardless of the device or communication protocol that is used to communicate with the IMD 10', the IMD 10' may send communications to the authenticating device that cause the authenticating device to present an interface that indicates that the IMD 10' is being prevented from communicating via the network 100 and enables the patient to enter authenticating information such as a username and password to complete the secure authentication process.

If the short-range RF communication circuitry 190 is disabled altogether, secure authentication may be accomplished via an external device that communicates with the IMD 10' via inductive-based communications (e.g., the external controller 40 or CP system 80). As noted above, such communications are considered secure because they are conducted over a short distance. Here again, the patient may be required to enter authenticating information such as a username and password to complete the secure authentication.

If both short-range RF communication circuitry 190 and inductive communication circuitry 130 are disabled, secure authentication may be accomplished by placing the magnet 92 in close proximity to the IMD 10' so that it can be recognized by the sensor 33. In this arrangement, the secure authentication may require sequential steps. For example, use of the magnet 92 may re-enable the inductive communication circuitry 130 such that the patient can then complete the above-described authentication using an inductive-based communicator such as the external controller 40 or the CP system 80. While proximity detection using the magnet 92 is described, other types of proximity detectors might alternatively be used.

In one embodiment, the secure authentication process may require that the IMD 10' obtain the most current firmware directly from a trusted device (i.e., not via the network 100). The trusted device may be, for example, the device that is providing the secure authentication. In such an embodiment, the trusted device (e.g., external controller 40) may request, from the IMD 10', the identifier 148 of the firmware that is installed on the IMD 10' and may compare that identifier to the identifier 146 of the firmware that is available from the server 110. If the identifiers match, the secure authentication process is complete. However, if the identifiers do not match, the trusted device may obtain the most current firmware from the server 110 itself and may communicate the obtained firmware to the IMD 10'. In this way, the authenticity of the firmware can be verified by the trusted device and the IMD 10' may be prevented from communicating via the network 100 until it can be ensured that it has the most current firmware.

Once the secure authentication process is completed, the IMD's ability to communicate via the network 100 is re-enabled (222) and the security routine 200 again evaluates whether the IMD 10' is capable of communicating via the network 100. In one embodiment, the IMD 10' may initially only attempt to communicate via the network 100 through the device that provided the secure authentication. For example, if the secure authentication is provided through the external controller 40, the IMD 10' may be required to proceed through the steps of the security routine 200 through the external controller 40's connection to the network 100 in order to reset the communication timer, and, if the connection between the external controller 40 and the IMD 10' is lost, the security routine 200 may require the secure authentication process to be repeated.

In an alternative embodiment, the IMD 10' may not be required to communicate through the device that provided the secure authentication. Rather, when the secure authentication is completed, the communication timer may be set to a short time period (e.g., 3 hours) during which the IMD's communication capabilities are fully enabled. In one embodiment, the time period may be selectable by the patient through the authentication interface. During this short time period, it must be confirmed that the most current firmware is installed on the IMD 10' or the communication timer will expire and the secure authentication process will need to be repeated.

Figure 6:
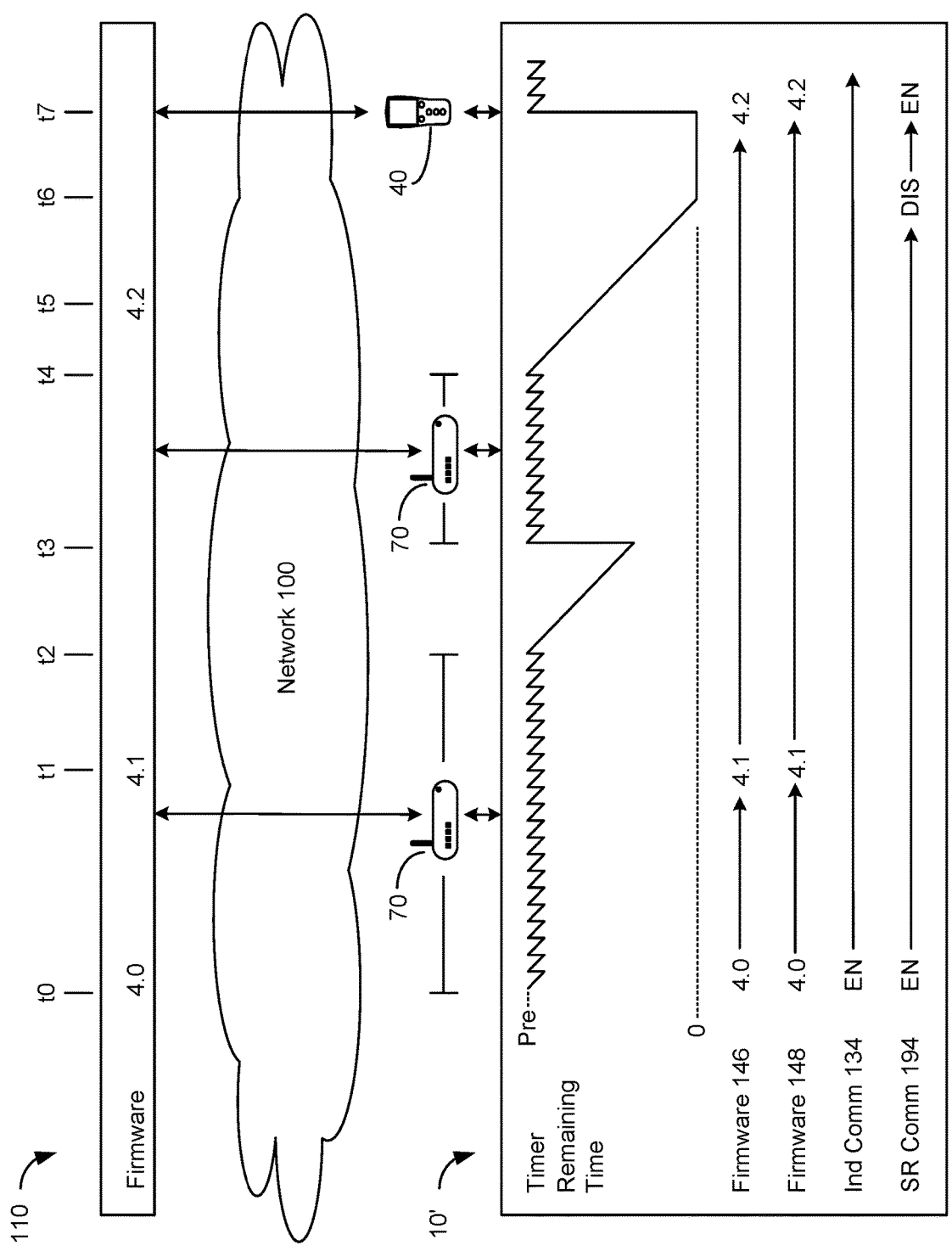
FIG. 6 is a timing diagram that illustrates an example execution of the security routine for various communication states of an IMD in accordance with an aspect of the disclosure.

FIG. 6 illustrates an example implementation of the security routine 200 with the IMD 10' in various communication states over time. At time t0, the IMD 10' is connected to the network 100 through the wireless router 70. The server 110 is accessible to the IMD 10' via the connection of both devices to the network 100, and the latest version of the firmware that is stored on the server 110 (version 4.0) has been installed on the IMD 10'. Between time t0 and t1, the IMD 10' continues to be connected to the network 100 via the wireless router 70, and, as a result, the communications timer is continuously reset (i.e., the remaining time is continuously updated to the preset value). At time t1, a new firmware version (version 4.1) is made available on the server 110. As described above, this new version of the firmware may be made available in order to eliminate an identified security vulnerability that is present in earlier versions of the firmware. Because the IMD 10' is connected to the network 100, it receives the identifier 146 of the new firmware shortly after it is made available at time t1, and the identifier 146 is stored in the memory 140. Because the identifier 146 does not match the local firmware identifier 148, the IMD 10' downloads and installs the most current firmware (version 4.1) from the server 110 over the network 100. After the installation of the firmware, the local firmware identifier 148 is updated to reflect the installation of the new firmware (version 4.1) such that the local identifier 148 again matches the network identifier 146.

The IMD 10' continues to be connected to the network 100 between times t1 and t2, so the communications timer is continuously reset. At time t2, the connection between the IMD 10' and the network 100 is lost. Because the IMD 10' is not capable of communicating via the network 100, the communication timer continues to run (i.e., the remaining time is continuously decremented). Eventually, at time t3, before the communication timer expires, the connection between the IMD 10' and the network 100 is re-established, so the communication timer is again reset and the remaining time value is restored to the preset value. The connection between the IMD 10' and the network 100 remains intact between time t3 and t4, and the communication timer is again continuously reset with each execution of the security routine 200.

At time t4, the connection between the IMD 10' and the network 100 is again lost, and the communication timer once again continues to run. At time t5, a new version of the firmware (version 4.2) is made available on the server 110. However, because the IMD 10' is not capable of communicating via the network 100, it cannot receive the update. Eventually, at time t6, the communication timer expires (i.e., the remaining time equals zero), and, as a result, the microcontroller 34' prevents the IMD 10' from communicating via the network 100. In the illustrated embodiment, this is accomplished by disabling the short-range RF communication circuitry 190 via the control signal 194. In this state, the IMD 10' cannot establish a connection to the network 100, for example, via the wireless router 70, even if the IMD 10' would have otherwise been able to connect to the network 100. Thus, any malicious actor that might have gained access to the IMD 10' via the network 100 will be unable to communicate with the IMD 10' and thus unable to exploit any potential vulnerabilities such as those that were corrected through the release of the version 4.2 firmware. Although the short-range RF communication circuitry 190 is disabled in this state, the inductive communication circuitry 130 remains enabled (or at least periodically enabled in accordance with its usual operation as described above). When the IMD 10' establishes communications with the external controller 40 at time t7 (via inductive communication link 42), the IMD 10' may initially send a message that causes the external controller 40 to present an interface that indicates that the IMD 10' is being prevented from communicating via the network 100. The interface may additionally present an authentication form that enables the user to enter authentication information via the external controller 40. In the illustrated embodiment, after the secure authentication is completed using the external controller 40, the external controller 40 acts as a bridge that provides a connection between the network 100 and the IMD 10'. Using this connection, the IMD 10' retrieves the identifier 146 of the most current firmware from the server 110 (version 4.2), and, because the identifier 146 does not match the local identifier 148 of the firmware that is installed on the IMD 10', the IMD 10' downloads and installs the most recent firmware from the server 110 (through the external controller 40). When the installed firmware is verified as matching the most recent firmware, the communication timer 144 is reset to the preset value and any remaining network communication restrictions are removed (e.g., the short-range RF communication circuitry 190 is re-enabled).

While the illustrated embodiment shows that the external controller 40 is used to provide the secure authentication as well as the link to the network 100, this function could be performed by a different trusted device as described above. Moreover, and as also described above, the secure authentication by the external controller 40 (or another trusted device) may alternatively result in the elimination of all network connectivity restrictions for a shortened time period within which the IMD 10' must establish a full reset of the communication timer to the preset value. In this arrangement, if the full reset is not accomplished during the shortened time period, the IMD 10' will again be prevented from communicating via the network 100 and the secure authentication process will need to be repeated.

As illustrated by the example in FIG. 6, the security routine 200 assumes that an IMD 10' that has not connected to the network 100 for an extended period of time may have security vulnerabilities and it prevents the exploitation of such vulnerabilities by preventing the vulnerable IMD 10' from communicating via the network 100 until it has installed the necessary security updates.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. An implantable medical device (IMD), comprising:
  communication circuitry that enables the IMD to communicate via a communication network; and
  control circuitry configured to execute program code to cause the control circuitry to:
    determine whether the IMD is capable of communicating via the communication network;
    request, from a computing device connected to the communication network, a first identifier of current firmware that is stored on the computing device when it is determined that the IMD is capable of communicating via the communication network;
    compare the first identifier to a second identifier of firmware that is installed on the IMD;
    prior to expiration of a communication timer, reset the communication timer when the first identifier matches the second identifier;
    prior to expiration of the communication timer, download the current firmware from the computing device to the IMD when it is determined that the first identifier does not match the second identifier, and reset the communication timer; and
    after expiration of the communication timer, prevent the IMD from communicating via the communication network.

2. The IMD of claim 1, wherein the communication circuitry comprises inductive communication circuitry and short-range RF communication circuitry.

3. The IMD of claim 2, wherein the program code to cause the control circuitry to prevent the IMD from communicating via the communication network comprises program code to cause the control circuitry to disable the short-range RF communication circuitry.

4. The IMD of claim 1, wherein the program code to cause the control circuitry to prevent the IMD from communicating via the communication network comprises program code to cause the control circuitry to prevent the IMD from communicating via the communication network until a secure authentication process is performed.

5. The IMD of claim 4, wherein the secure authentication process comprises communicating with an external device via magnetic inductive coupling.

6. The IMD of claim 5, wherein the external device provides a connection between the IMD and the communication network.

7. The IMD of claim 4, wherein the secure authentication process comprises placing a magnet in proximity to the IMD.

8. The IMD of claim 1, wherein the program code to cause the control circuitry to determine whether the IMD is capable of communicating via the communication network comprises program code to cause the control circuitry to send a request to the computing device.

9. The IMD of claim 1, wherein the communication network is an internet.

10. The IMD of claim 9, wherein the computing device is a server that is maintained by a manufacturer of the IMD.

11. A method to ensure security of an implantable medical device (IMD), comprising:
  initiating a communication timer in the IMD;
  determining whether the IMD is capable of communicating via a communication network over which it can receive security updates;
  requesting, from a computing device connected to the communication network, a first identifier of current firmware that is stored on the computing device when it is determined that the IMD is capable of communicating via the communication network;
  comparing the first identifier to a second identifier of firmware that is installed on the IMD;
  prior to expiration of the communication timer, resetting the communication timer when the first identifier matches the second identifier;
  prior to expiration of the communication timer, downloading the current firmware from the computing device to the IMD when it is determined that the first identifier does not match the second identifier, and resetting the communication timer; and
  after expiration of the communication timer, preventing the IMD from communicating via the communication network.

12. The method of claim 11, wherein the IMD comprises inductive communication circuitry and short-range RF communication circuitry.

13. The method of claim 12, wherein preventing the IMD from communicating via the communication network comprises disabling the short-range RF communication circuitry.

14. The method of claim 11, wherein preventing the IMD from communicating via the communication network comprises preventing the IMD from communicating via the communication network until a secure authentication process is performed.

15. The method of claim 14, wherein the secure authentication process comprises communicating with an external device via magnetic inductive coupling.

16. The method of claim 15, wherein the external device provides a connection between the IMD and the communication network.

17. The method of claim 14, wherein the secure authentication process comprises placing a magnet in proximity to the IMD.

18. A system, comprising:
  a server connected to a communication network; and
  an implantable medical device, comprising:
    communication circuitry that enables the IMD to communicate with the server via the communication network; and
    control circuitry configured to execute program code to cause the control circuitry to:
      determine whether the IMD is capable of communicating with the server;
      request a first identifier of current firmware that is stored on the server when it is determined that the IMD is capable of communicating with the server;
      compare the first identifier to a second identifier of firmware that is installed on the IMD;
    prior to expiration of a communication timer, reset the communication timer when the first identifier matches the second identifier;
    prior to expiration of the communication timer, download the current firmware from the computing device to the IMD when it is determined that the first identifier does not match the second identifier, and reset the communication timer; and
    after expiration of the communication timer, prevent the IMD from communicating via the communication network.

\* \* \* \* \*